(12) United States Patent
Lee et al.

(10) Patent No.: US 8,753,870 B2
(45) Date of Patent: Jun. 17, 2014

(54) DEVICE FOR DETECTING AND SEPARATING TARGET MOLECULES AND METHOD FOR DETECTING AND SEPARATING TARGET MOLECULES BY USING THE SAME

(75) Inventors: Hun-joo Lee, Hwaseong-si (KR); Jeong-gun Lee, Seoul (KR); Jeong-woo Choi, Seoul (KR); Yeon-jeong Kim, Yongin-si (KR); Jong-myeon Park, Incheon (KR); Mi-jeong Song, Suwon-si (KR); Jin-mi Oh, Suwon-si (KR)

(73) Assignees: Samsung Electronics Co., Ltd., Suwon-Si (KR); Industry -University Coorperation Foundation Sogang University, Seoul (KR)

( * ) Notice: Subject to any disclaimer, the term of this patent is extended or adjusted under 35 U.S.C. 154(b) by 0 days.

(21) Appl. No.: 13/605,787

(22) Filed: Sep. 6, 2012

(65) Prior Publication Data
US 2013/0137092 A1 May 30, 2013

(30) Foreign Application Priority Data

Nov. 29, 2011 (KR) .......................... 10-2011-0126281

(51) Int. Cl.
| | | |
|---|---|---|
| *C12M 1/00* | (2006.01) | |
| *C12Q 1/68* | (2006.01) | |
| *G01N 33/53* | (2006.01) | |
| *C12M 1/34* | (2006.01) | |
| *C12M 3/00* | (2006.01) | |
| *G01N 30/96* | (2006.01) | |
| *C07H 21/02* | (2006.01) | |

(52) U.S. Cl.
USPC ....... 435/283.1; 435/6.1; 435/7.1; 435/287.1; 435/287.2; 422/69; 536/23.1

(58) Field of Classification Search
USPC .................. 435/6.1, 7.1, 283.1, 287.1, 287.2; 422/69; 536/23.1
See application file for complete search history.

(56) References Cited

U.S. PATENT DOCUMENTS

| | | | |
|---|---|---|---|
| 6,962,786 B2 | 11/2005 | Mirkin et al. | |
| 7,323,309 B2 | 1/2008 | Mirkin et al. | |
| 7,776,547 B2 | 8/2010 | Roth et al. | |
| 7,829,350 B2 | 11/2010 | Josephson et al. | |
| 2003/0054376 A1* | 3/2003 | Mullis et al. | 435/6 |
| 2006/0046313 A1 | 3/2006 | Roth et al. | |
| 2007/0026381 A1 | 2/2007 | Huang et al. | |
| 2009/0188864 A1 | 7/2009 | Zheng et al. | |
| 2010/0285581 A1 | 11/2010 | Hauch et al. | |
| 2011/0104718 A1 | 5/2011 | Rao et al. | |

OTHER PUBLICATIONS

Ho et al, DNA as a Force Sensor in an Aptamer-Based Biochip for Adenosine, 2009, Ananl. Chem., 81, 3159-3164.*
Sieuwerts et al, "Anti-Epithelial Cell Adhesion Molecule Antibodies and the Detection of Circulating Normal-Like Breast Tumor Cells", *J. Natl Cancer Inst.*, 101:61-66 (2009).

* cited by examiner

*Primary Examiner* — Narayan Bhat
(74) *Attorney, Agent, or Firm* — Leydig, Voit & Mayer, Ltd.

(57) ABSTRACT

A device, system, and method for detecting or separating target molecules allowing efficient detection even when only a small amount of target molecules or target cells are included in a sample involving the use of a target molecule linkage portion, a signal production portion, and first and second separation portions.

10 Claims, 7 Drawing Sheets

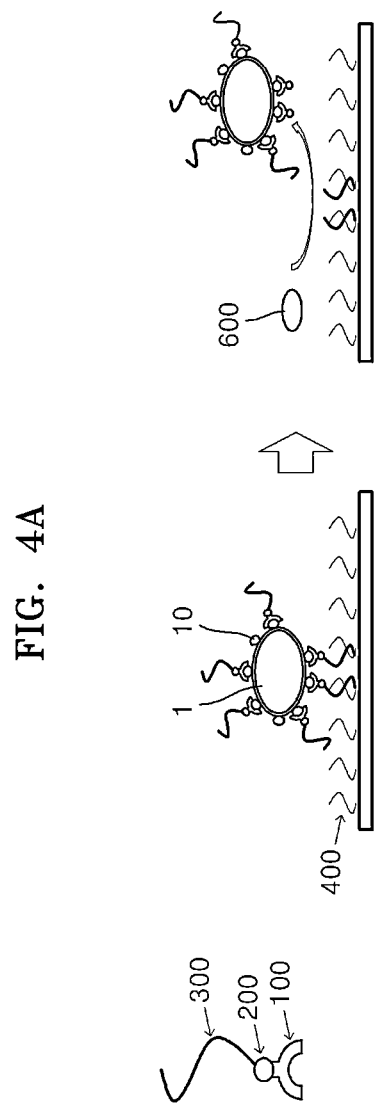

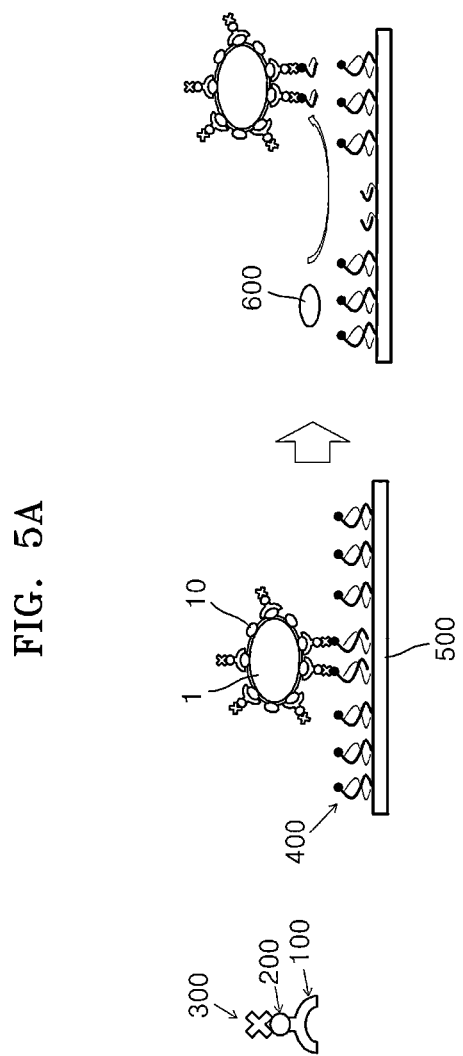

DEVICE FOR DETECTING AND SEPARATING TARGET MOLECULES AND METHOD FOR DETECTING AND SEPARATING TARGET MOLECULES BY USING THE SAME

CROSS-REFERENCE TO RELATED APPLICATIONS

This application claims the benefit of Korean Patent Application No. 10-2011-0126281, filed on Nov. 29, 2011, in the Korean Intellectual Property Office, the disclosure of which is incorporated herein in its entirety by reference.

BACKGROUND

Technologies for detecting or separating target molecules in a sample are used in various fields. Recently, a method of detecting or separating tumor cells from the blood has attracted much attention. For example, separating tumor cells from the blood and detecting a protein expressed from tumor cells are very important in diagnosis and treatment. Particular cells may be separated from a sample by using a magnetic separation method using a magnetic field, a three-dimensional filler method using a maximized binding surface area, a filter method using a size difference, etc. Tumor cells, however, are present in a very small amount in the blood, and according to their kinds, the kind or amount of protein expressed on their surfaces may vary. Accordingly, existing methods have limitations. Also, for use in additional assays, such as genetic variations, cytoplasm experiments, or culture experiments, which follow the separation and detection of the tumor cells, cells need to be separated intact under mild conditions. Thus, there is a need to develop a method of detecting target molecules or target cells in a sample or separating target molecules or target cells intact from a sample for use in additional assays.

SUMMARY

Provided are devices and systems for efficiently detecting or separating a small amount of target molecules or target cells included in a sample, and detection and separation methods using the devices or systems.

Provided is a device or system for detecting or separating target molecules, wherein the device or system includes: a target molecule linkage portion that is specifically linkable to target molecules; a signal production portion that is linked to the target molecule linkage portion and produces a detectable signal; a first separation portion linked to the signal production portion; and a second separation portion that is fixed on a solid support and is specifically linkable to the first separation portion, wherein the first separation portion and the second separation portion have a cleavage region when linked to each other.

Provided is a method of detecting or separating target molecules using the device or system provided herein. The method includes providing a sample including target molecules; introducing the sample to a device that includes a target molecule linkage portion that is specifically linkable to the target molecules, a signal production portion that is linked to the target molecule linkage portion and produces a detectable signal, a first separation portion linked to the signal production portion, and a second separation portion that is fixed on a solid support and is specifically linkable to the first separation portion, wherein the first separation portion and the second separation portion have a cleavage region when linked to each other; linking the target molecules and the target molecule linkage portion, followed by detecting a detection signal produced from the signal production portion; linking the first separation portion and the second separation portion, followed by washing to remove a non-linked material to separate the target molecules from the sample; and cleaving the cleavage region of the first and second separation portions, followed by collecting the result cleaved portion to separate the target molecules from the solid support.

Herein, the target molecules may include a protein present on surfaces of target cells. The target cells may include a circulating tumor cell (CTC).

The target molecule linkage portion may include an antibody, polypeptide, or aptamer, which are specifically linkable to the target molecule. Molecules, compounds, and other materials are specifically linkable with a binding partner if they bind to the binding partner with greater affinity as compared to other non-binding partner molecules, compounds, or materials. In other words, they discriminately or specifically bind their binding partners.

The signal production portion may be selected from the group consisting of dye, dye-labeled glass beads, dye-labeled polymer beads, Q-dot, Au, Ag, Cu, silica, and magnetic beads.

The detectable signal may be selected from the group consisting of a fluorescent signal, a luminescent signal, a color signal, a Raman signal, and a surface-enhanced Raman scattering (SERS) signal.

The first separation portion and the second separation portion may respectively be a single-stranded nucleic acid, and a single-stranded nucleic acid that is complementary thereto; biotin, and a structure including streptavidin that specifically binds to the biotin and a double-stranded nucleic acid linked to the streptavidin; streptavidin, and a structure including biotin that specifically binds to the streptavidin and a double-stranded nucleic acid linked to the biotin; a material that is the same material as a target molecule linkage portion, and a structure including a material that is the same material as a target molecule and a double-stranded nucleic acid linked to the material; or a first antibody or antigen, and a structure including a second antibody or antigen that specifically binds to the first antibody or antigen and a double-stranded nucleic acid linked to the second antibody or antigen.

A double-stranded nucleic acid region formed when the first separation portion is linked to the second separation portion may include a region that is cleavable by a cleavage enzyme.

The cleavage enzyme may be selected from the group consisting of DNase, EcoRI, BamHI, HindIII, Kpn I, Not I, Pst I, Sma I, and Alu I.

BRIEF DESCRIPTION OF THE DRAWINGS

These and/or other aspects will become apparent and more readily appreciated from the following description of the embodiments, taken in conjunction with the accompanying drawings in which:

FIGS. 4A to 4C show images illustrating a method of detecting or separating target molecules by using a device or system for detecting or separating target molecules, according to an embodiment of the present invention, and separation results; and FIGS. 5A to 5C show images illustrating a method of detecting or separating target molecules by using a device or system for detecting or separating target molecules, according to another embodiment of the present invention, and separation results.

DETAILED DESCRIPTION

Figure 1:
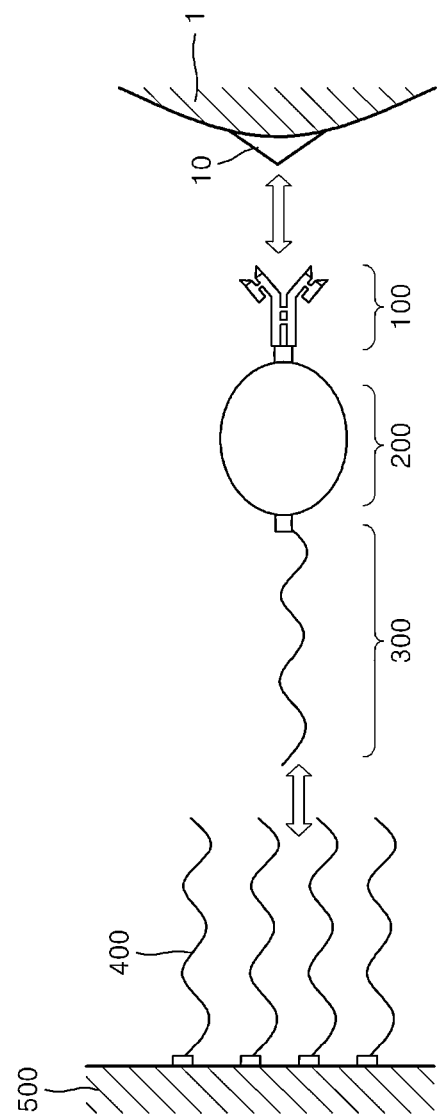
FIG. 1 is a conceptual diagram of a device or system for detecting or separating a target molecule, according to an embodiment of the present invention, illustrating elements of the device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, embodiments of the present invention are described in detail below.

The following description is for illustrative purpose only, and does not restrict the scope for which protection is searched.

FIG. 1 is a conceptual diagram of a device or system for detecting or separating a target molecule 10, according to an embodiment of the present invention.

The device or system according to the present embodiment includes a target molecule linkage portion 100 that is specifically linkable to the target molecule 10; a signal production portion 200 that is linked to the target molecule linkage portion 100 and produces a detectable signal; a first separation portion 300 linked to the signal production portion 200; and a second separation portion 400 that is fixed on a solid support 500 and is specifically linkable to the first separation portion 300, wherein the first separation portion 300 and the second separation portion 400 have a cleavage region when they are linked.

The device or system is for detecting or separating target molecules present inside a sample. The target molecules may include a biomolecular material, such as protein, nucleic acid, cells, organelles, bacteria, and viruses, but is not limited thereto. Referring to FIG. 1, the target molecule 10 may be a protein present on the surface of a target cell 1. The target cell 1 may be a circulating tumor cell (CTC). For example, a breast tumor cell, which is a kind of CTC, may have a subtype (Normal-like, Basal-like, Luminal, HER2-Positive) that is determined according to a protein expressed on the surface of a cell, such as ER, PR, HER2, CK5/6 etc. The kind or amount of the protein on the surface of a cell may significantly vary according to the subtype. Accordingly, separating and detecting breast tumor cells included in a blood sample may be efficiently performed using a particular protein that expresses on surfaces of the breast tumor cells as target molecules.

The device or system includes a target molecule linkage portion 100, which is specifically linked or bound to the target molecule 10 so as to be able to detect specifically and distinguish the target molecule 10 included in a sample from other molecules or compounds that may be in the sample. For example, if the target molecule 10 is an antigen, the target molecule linkage portion 100 may be an antibody that is specific to (specifically linkable to) the antigen. Referring to FIG. 1, the target molecule linkage portion 100 may be antibody, polypeptide, or aptamer, which are specifically linkable to the target molecule 10, for example, a protein expressed on the surface of a cell. However, the target molecule linkage portion 100 may not be limited as long as the target molecule linkage portion 100 is specifically linkable to any target molecule. As used herein, the term antibody encompasses antibody fragments (e.g., Fab, ScFv, single domain, etc.).

The device or system includes the signal production portion 200 connected to the target molecule linkage portion 100. The signal production portion 200 is used to confirm whether the target molecule 10 included in a sample is specifically linked to the target molecule linkage portion 100, and may not be limited as long as the signal production portion 200 produces a detectable signal. Also, the detectable signal may be a fluorescent signal, a luminescent signal, a color signal, a Raman signal, or a surface-enhanced Raman scattering (SERS) signal, but is not limited thereto. For example, the signal production portion 200 may be dye, dye-labeled glass beads, dye-labeled polymer beads, Quantum dot (Q-dot), gold (Au) particles, silver (Ag) particles, copper (Cu) particles, silica, or magnetic beads. Also, the linkage between the target molecule linkage portion 100 and the signal production portion 200 may be easily embodied by one of ordinary skill in the art through any known method, such as complementary binding between streptavidin and biotin.

The device or system may include the first separation portion 300 and the second separation portion 400 to perform an additional assay after the target molecule 10 included in a sample is detected. The additional assay may include separation of the target molecule 10, a polymerization enzyme chain reaction (PCR) of the target molecule 10, cell culture, etc. The first separation portion 300 may be linked to the signal production portion 200, the second separation portion 400 may be fixed on the solid support 500, the first separation portion 300 may be mutually specifically linked to the second separation portion 400, and each of the first separation portion 300 and the second separation portion 400 includes a cleavage region when in a linked state. The solid support 500 may be glass, silicon, synthetic resin, or the like, but is not limited thereto. Also, the linkage between the signal production portion 200 and the first separation portion 300 may be easily embodied by one of ordinary skill in the art through any known method, such as complementary binding between streptavidin and biotin. The fixing of the second separation portion 400 on the solid support 500 may be easily embodied by one of ordinary skill in the art through any known method, such as a self-assembled monolayer (SAM) coating method and an amine nucleic acid fixation method.

Figure 2:
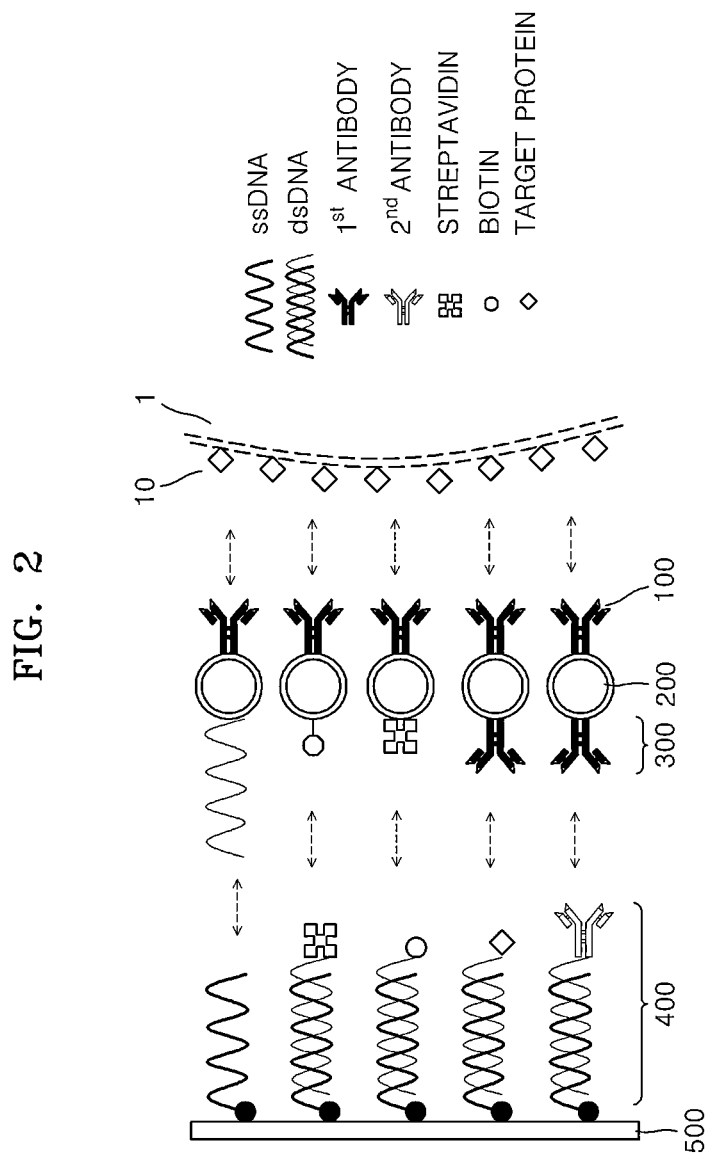
FIG. 2 illustrates examples of constituting elements of a device or system for detecting or separating a target molecule, according to an embodiment of the present invention.

FIG. 2 illustrates examples of elements of a device or system for detecting or separating a target molecule 10, according to an embodiment of the present invention. Referring to FIG. 2, the device or system according to the present embodiment includes a target molecule linkage portion 100 that is linkable to the target molecule 10 expressed on the surface of a target cell 1, a signal production portion 200 linked to the target molecule linkage portion 100, a first separation portion 300 linked to the signal production portion 200, and a second separation portion 400 that is linked to a solid support 500. Also, referring to FIG. 2, the first separation portion 300 and the second separation portion 400 may respectively be a single-stranded nucleic acid and a single-stranded nucleic acid that is complementary thereto; biotin, and a structure including streptavidin that specifically binds to the biotin and a double-stranded nucleic acid linked to the streptavidin; streptavidin, and a structure including biotin that specifically binds to the streptavidin and a double-stranded nucleic acid linked to the biotin; a material that is the same material as a target molecule linkage portion, and a structure including a material that is the same material as a target molecule and a double-stranded nucleic acid linked to the material; or a first antibody or antigen and a structure including a second antibody or antigen that specifically binds to the first antibody or antigen and a double-stranded nucleic acid linked to the second antibody or antigen, but is not limited thereto. Owing to the specific linkage between the first separation portion 300 and the second separation portion 400, only the target molecule 10 specifically linked to the target molecule linkage portion 100 may be separated from the sample. Also, the cleavage region may be a double-stranded nucleic acid region formed when the first separation portion 300 is linked to the second separation portion 400 and may be cleavable by a cleavage enzyme, but is not limited thereto. In this regard, the cleavage enzyme may be DNase, EcoRI, BamHI, HindIII, Kpn I, Not I, Pst I, Sma I, or Alu I.

A method of detecting or separating the target molecule 10 by using a device or system according to an embodiment of the present invention includes providing a sample including the target molecule 10; and introducing the sample to the device or system that includes the target molecule linkage portion 100 that is specifically linkable to the target molecule 10; the signal production portion 200 that is linked to the target molecule linkage portion 100 and produces a detectable signal; the first separation portion 300 linked to the signal production portion 200; and the second separation portion 400 that is fixed on the solid support 500 and is specifically linkable to the first separation portion 300, wherein the first separation portion 300 and the second separation portion 400 have a cleavage region when they are linked. The sample may include, in addition to the target molecule 10, non-target molecules.

Also, the method includes linking the target molecule 10 and the target molecule linkage portion 100, followed by linking the first separation portion 300 and the second separation portion 400; detecting a detectable signal produced from the signal production portion 200 after the linking; washing to remove a non-linked molecule after the linking; and separating cleaved portions after the cleaving. In this case, the target molecule 10 may be qualitatively or quantitatively assayed using a signal produced from the signal production portion 200, and also, may be isolated by removing non-target molecules from the sample.

Then, the cleavage region of the first and second separation portions 300 and 400 is cleaved, and the resultant cleaved portion is collected to separate the target molecule 10 from the solid support 500. In this case, the target molecule 10 included in the cleaved portion is separated from the solid support 500 under mild conditions, thereby enabling additional assays of the target molecule 10.

Accordingly, when devices or systems and methods according to embodiments of the present invention are used, however small amounts of target molecules included in a sample are, the detection and separation thereof may be easily performed. Furthermore, the target molecules 10 are separated from the solid support 500 under mild conditions, thereby enabling additional assays easily.

Example 1

Target Molecule Detection

MCF-7 cells, which are a kind of breast tumor cell, were used as target molecules. A biotinylated anti-EpCAM antibody was prepared as a target molecule linkage portion that is specifically linkable to the MCF-7 cells, streptavidin-coated Q-dot was prepared as a signal production portion, and a single-stranded DNA (5'-TGTCCAAGCTTACAAGCT-TACT-3') to which biotin was linked was used as a first separation portion. The biotinylated anti-EpCAM antibody, the streptavidin-coated Q-dot and biotin-linked single-stranded DNA were reacted at room temperature for about 1 hour, followed by centrifugal filtration, to prepare a first complex of target molecule linkage portion-signal production portion-first separation portion.

Also, a slide glass was used as a solid support, and the slide glass was treated with a Piranha solution, and 3-aminopropyltriethoxysilane (APTES) was coated thereon, followed by treatment of succinic anhydride. Thus, the slide glass with a carboxylic acid surface was prepared. Then, as a second separation portion, amine linked single-stranded DNA(5'-AT-GATAGGAGTAAGCTTGTAAGCTTGG-3') was used, and the second separation portion was linked to the carboxylic acid surface by EDC/NHS, thereby preparing a solid support on which the second separation portion was fixed.

In preparing the complex 1 of target molecule linkage portion-signal production portion-first separation portion, amounts of the signal production portion (streptavidin-coated Q-dot) and the first separation portion (biotin-linked single-stranded DNA) were maintained at 2 pmol and 200 pmol, respectively, and only an amount of the target molecule linkage portion was controlled to confirm a linkage with the target molecules (MCF-7 cell).

Figure 3:
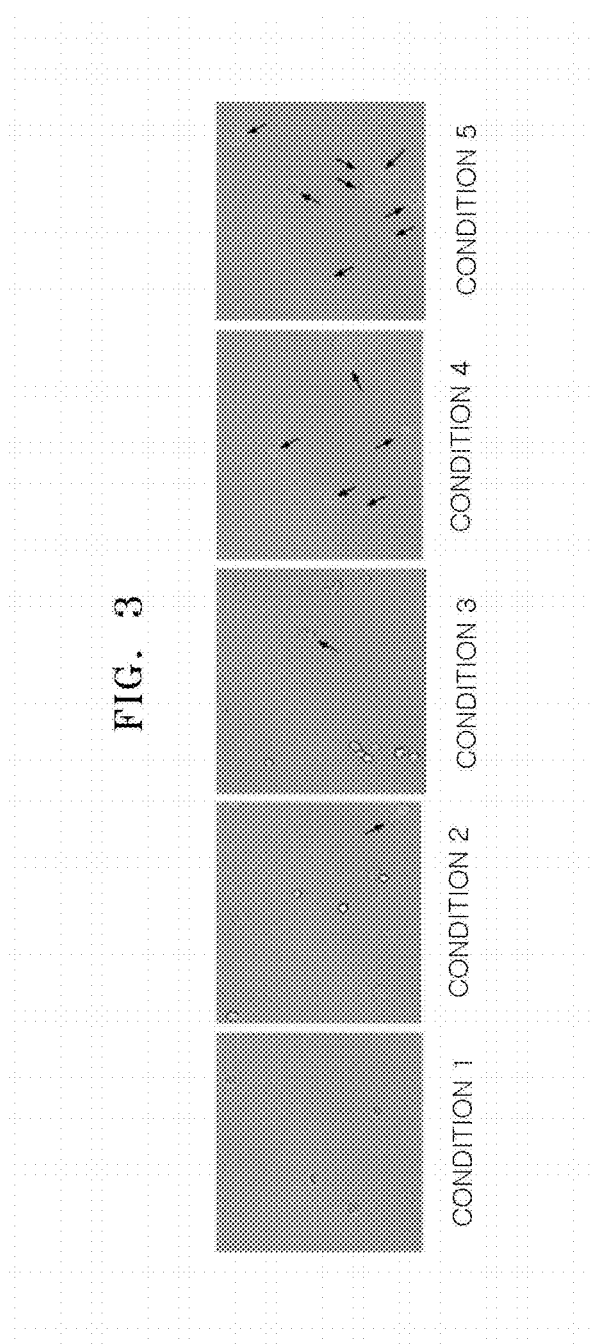
FIG. 3 shows images for confirming a linkage between a device or system for detecting or separating target molecules, according to an embodiment of the present invention, and target molecules (MCF-7 cells), wherein an amount of a material used as a target molecule linkage portion varies.

FIG. 3 shows images for confirming a linkage between a device for detecting or separating target molecules, according to an embodiment of the present invention, and target molecules (MCF-7 cells), wherein an amount of a material used as a target molecule linkage portion varies. Referring to FIG. 3, the amount of the target molecule linkage portion was 1 pmol in Condition 1; 2 pmol in Condition 2; 5 pmol in Condition 3; 10 pmol in Condition 4; and 5 pmol in Condition 5. As a result, the linkage was more clearly confirmed in Conditions 4 and 5.

Example 2

Target Molecule Detection and Separation 1

Figure 4B:
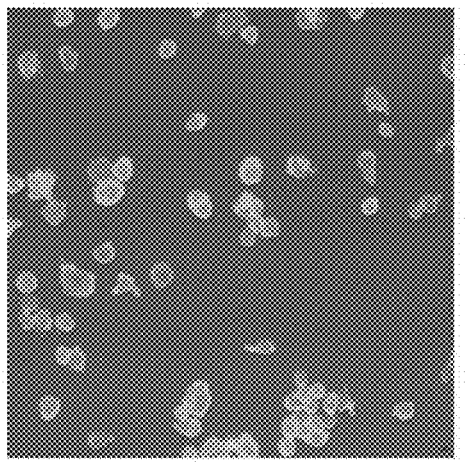
Figure 4C:
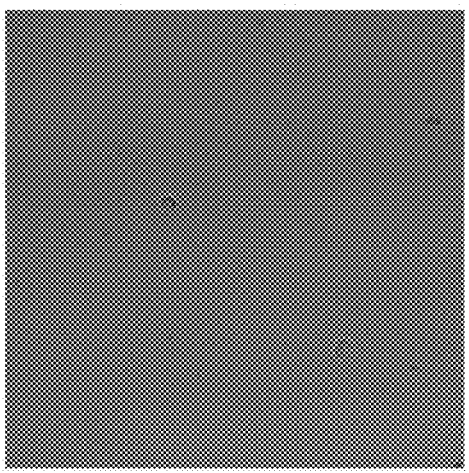

FIGS. 4A to 4C show images illustrating a method of detecting or separating target molecules by using a device for detecting or separating target molecules, according to an embodiment of the present invention, and separation results. In detail, FIG. 4A is a schematic view illustrating a process of detecting or separating MCF-7 cells, and FIGS. 4B and 4C show images of the result of each step of the process.

The complex 1 of target molecule linkage portion 100-signal production portion 200-first separation portion 300 prepared according to Example 1 was introduced to a solid support on which the second separation portion 400 was fixed, and MCF-7 cells were linked thereto. Then, the first separation portion 300 was linked to the second separation portion 400, followed by washing the solid support with 2×SSPE buffer. Then, a signal produced from the signal production portion 200 was measured (see illustrations on the left side of the arrow on FIG. 4A, and the image of FIG. 4B). Thereafter, the cleavage region of the first and second separation portions 300 and 400 linked to each other was cleaved with HindIII as a cleavage enzyme to collect a cleaved region (including MCF-7 cells), and the state of the solid support was confirmed (see the illustration on the right side of the arrow on FIG. 4A, and FIG. 4C). Referring to FIG. 4B, it was confirmed that MCF-7 cells were detected and separated, and referring to FIG. 4C, it was confirmed that MCF-7 cells were removed from the solid support.

Example 3

Target Molecule Detection and Separation 2

Figure 5B:
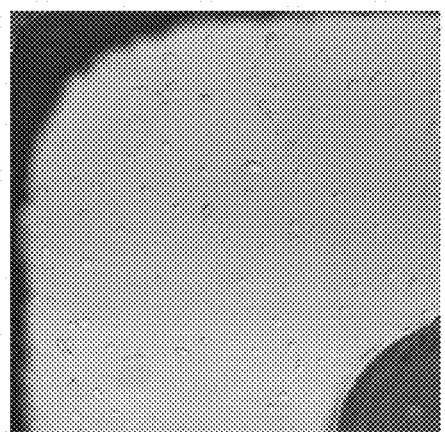
Figure 5C:

FIGS. 5A to 5C show images illustrating a method of detecting or separating target molecules by using a device for detecting or separating target molecules, according to another embodiment of the present invention, and separation results thereby. In detail, FIG. 5A is a schematic view illustrating a process of detecting or separating MCF-7 cells, and FIGS. 5B and 5C show images of the result of each step of the process.

A device for detecting or separating target molecules used in this experiment was the same as the device used in Example 2, except that streptavidin was used as the first separation portion 300 in the complex 1 of target molecule linkage portion 100-signal production portion 200-first separation portion 300, a double-stranded DNA linked to biotin that is binding specifically to the streptavidin was used as the second separation portion 400, and a microchannel was used as a solid support.

The complex 1 of target molecule linkage portion 100-signal production portion 200-first separation portion 300 was introduced to a solid support on which the second separation portion 400 was fixed, and MCF-7 cells were linked thereto. Then, the first separation portion 300 was linked to the second separation portion 400, followed by washing the solid support with 2×SSPE buffer. Then, a signal produced from the signal production portion 200 was measured (see illustrations on the left side of the arrow on FIG. 5A, and the image of FIG. 5B). Thereafter, the cleavage region of the first separation portion 300 and second separation portions 400 linked to each other was cleaved by HindIII as a cleavage enzyme to collect a cleaved region (including MCF-7 cells), and the state of the solid support was confirmed (see the illustration on the right side of the arrow on FIG. 5A, and FIG. 5C). Referring to FIG. 5B, it was confirmed that MCF-7 cells were detected and separated, and referring to FIG. 5C, it was confirmed that MCF-7 cells were removed from the solid support.

As described above, according to devices for detecting or separating target molecules and methods of detecting or separating target molecules by using the devices, according to the above embodiments of the present invention, a small amount of target molecules or target cells included in a sample may be efficiently detected or separated from a sample.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A device for detecting or separating target molecules, the device comprising: a target molecule linkage portion that is specifically linkable to a target molecule; a signal production portion that is linked to the target molecule linkage portion and produces a detectable signal; a first separation portion linked to the signal production portion; and a second separation portion that is fixed on a solid support and is specifically linkable to the first separation portion, wherein the first separation portion and the second separation portion have an enzyme cleavage region when linked to each other and configured to release the signal production portion, target molecule linkage portion, and any linked target molecule from the support upon cleavage by an enzyme; wherein the first separation portion and second separation portion are between the solid support and the signal production portion, and the signal production portion is between the first separation portion and the target molecule linkage portion.

2. The device of claim 1, wherein the target molecules are located on surfaces of target cells.

3. The device of claim 2, wherein the target cells comprise circulating tumor cells.

4. The device of claim 2, wherein the target molecule linkage portion comprises an antibody, a polypeptide, or an aptamer, which specifically binds a target protein.

5. The device of claim 1, wherein the signal production portion comprises one or more dyes, dye-labeled glass beads, dye-labeled polymer beads, quantum dots (Q-dot), gold (Au) particles, silver (Ag) particles, copper (Cu) particles, silica particles, or magnetic beads.

6. The device of claim 1, wherein the detectable signal comprises a fluorescent signal, a luminescent signal, a color signal, a Raman signal, or a surface-enhanced Raman scattering (SERS) signal.

7. The device of claim 1, wherein the first separation portion and the second separation portion, respectively, comprise: a single-stranded nucleic acid and a single-stranded nucleic acid that is complementary thereto; biotin, and a structure comprising streptavidin that specifically binds to the biotin and a double-stranded nucleic acid linked to the streptavidin; streptavidin, and a structure comprising biotin that specifically binds to the streptavidin and a double-stranded nucleic acid linked to the biotin; a material or compound that is identical to the target molecule linkage portion, and a structure comprising a molecule identical to the target molecule and a double-stranded nucleic acid linked to molecule; or a first antibody or antigen, and a structure comprising a second antibody or antigen that specifically binds to the first antibody or antigen and a double-stranded nucleic acid linked to the second antibody or antigen.

8. The device of claim 7, wherein when the first separation portion is linked to the second separation portion, a double stranded nucleic acid region is formed that is cleavable by a cleavage enzyme.

9. The device of claim 8, wherein the cleavage enzyme is DNase, EcoRI, BamHI, Hind III, Kpn I, Not I, Pst I, Sma I, or Alu I.

10. A method of detecting or separating target molecules, the method comprising: providing a sample comprising the target molecules; introducing the sample to a device of claim 1; linking the target molecules to the target molecule linkage portion; detecting a signal produced from the signal production portion; linking the first separation portion to the second separation portion; washing to remove non-linked molecules thereby separating the target molecules from the sample; cleaving the cleavage region of the first and second separation portions by a cleavage enzyme; and collecting the cleaved portion to separate the target molecules from the solid support.

* * * * *